United States Patent [19]

Kimura

[11] Patent Number: 4,931,398

[45] Date of Patent: Jun. 5, 1990

[54] BACILLUS SUBTILIS STRAIN AND PREVENTION OF AFLATOXIN CONTAMINATION IN CEREALS AND NUTS

[75] Inventor: Norio Kimura, Yokohama, Japan

[73] Assignee: Morinaga & Co., Ltd., Tokyo, Japan

[21] Appl. No.: 146,680

[22] Filed: Jan. 21, 1988

[30] Foreign Application Priority Data

Feb. 5, 1987 [JP] Japan ................................ 62-25476
Jun. 23, 1987 [JP] Japan .............................. 62-155998

[51] Int. Cl.$^5$ ...................... C12N 1/20; C12N 15/00; A01C 1/00; A01N 25/00
[52] U.S. Cl. ................................. 435/252.5; 424/93; 435/252.1; 435/172.3; 47/58
[58] Field of Search ............... 424/93; 435/253, 252.5

[56] References Cited

U.S. PATENT DOCUMENTS 4,595,589  6/1986  Tahvonen ............................. 424/93

OTHER PUBLICATIONS

Sinclair, T. R. et al., *Agr. Res. Serv.* Progress Report Accession #0043946 (Dialog) Jul., 14, 1986.

Korean J. of Microbiology (1979) vol. 17 (1) p. 16–24, abstract only (English).
Korean J. of Microbiology (1979) vol. 17 (2), p. 72–80 abstract only (English).
Rev. Immunol. (1972) vol. 36 (1–2)p. 15–35, abstract only (English).
J. Sci. Fd Agric., vol. 27, 324–330 (1976).
Z. Lebensm, Unters. –Forsch., vol. 163, 39–43 (1977), English abstract only.
Phytopathology, vol. 70, No. 8, 761–764 (1980).
Journal of Food Protection, vol. 49, No. 7, 515–518 (1986).

*Primary Examiner*—Robin Teskin
*Assistant Examiner*—Beth A. Burrous
*Attorney, Agent, or Firm*—Nixon & Vanderhye

[57] ABSTRACT

A microbiological prevention of aflatoxin contamination in cereals and nuts is provided. *Bacillus subtilis* NK-330 and NK-C-3 effectively inhibit not only growth of aflatoxin-producing fungi including *Aspergillus flavus* and *Aspergillus parasiticus* but also production of aflatoxin by them.

5 Claims, No Drawings

BACILLUS SUBTILIS STRAIN AND PREVENTION OF AFLATOXIN CONTAMINATION IN CEREALS AND NUTS

FIELD OF THE INVENTION

This invention relates to a microbiological prevention of aflatoxin contamination in cereals and nuts, in particular, to certain strains of Bacillus subtilis capable of inhibiting growth of fungi which produce aflatoxin, hereinafter referred to as "aflatoxin-producing fungi", and moreover of suppressing production of aflatoxin by them. More specifically, the invention relates to Bacillus subtilis strains NK-330 and NK-C-3 and their variants.

BACKGROUND OF THE INVENTION

Aflatoxin is one of the most potent carcinogens among those hitherto known. Aflatoxin is a metabolite secreted by the aflatoxin-producing fungi such as Aspergillus flavus and Aspergillus parasiticus, and several homologues thereof including aflatoxin $B_1$ and aflatoxin $G_1$ are also known.

Among food cereals such as wheat, barley, rice, corn (maize), etc. and food nuts such as hazelnut, almond, Brazil nut, peanut, etc., those contaminated with the aflatoxin have been found (cf. Am. Assoc. Cereal Chemists Inc., 595(1974); Am. Assoc. Cereal Chemists Inc., 603(1975); JAOCS, 980A, December (1981); J. Agric. Food Chem., 26, 249 (1978); Dtsch Lebensm. Rudsch., 76, 47(1980); Lebensm. -Wiss. u. -Technol., 14, 252(1981)), and the aflatoxin-producing fungous microbes are supposed to possibly spread around the areas where these crops are cultivated and yielded. Since such cereals and nuts contaminated with the aflatoxin provide a serious health problem, a lot of countries strictly regulate the importation of the contaminated cereals and nuts so as not to enter their territories.

When the cereals and nuts are grown in a field infected with the aflatoxin-producing fungi, the possibility that the yielded cereals and nuts are as well contaminated with the aflatoxin is likely very high. Particularly, in tropical and subtropical zones quite many fields have been found to be infected and contaminated with those aflatoxin-producing fungi. It is an urgent measure to prevent the aflatoxin contamination in the cereals and nuts and to provide the cereals and nuts free from those carcinogenic aflatoxin.

It is known that the aflatoxin may be removed in soil (cf. Soil Sci. Soc. Am. J., 44, 1237 (1980)), and the adsorption of the aflatoxin to the soil and the participation of some microbes in the removal of the aflatoxin are supposed to be causes therefor. Further, it has been reported that many microbes may experimentally reduce the quantity of aflatoxin in an aqueous test solution into which the aflatoxin is dissolved (cf. J. Bact., 93, 464 (1967); J. gen. Microbiol., 54, 185 (1968); Naturwissenschaften, 62, 537 (1975); Proc. Japan. Assoc. Mycotoxicol., 12, 33 (1980)). Among those microbes, Flavobacterium aurantiacum, Bacillus megaterium, Corynebacterium rubrum, Penicillium islandicum, Stachybotrys lobulata, Cumminghamella echinulata, Streptococcus lactis and so on have hitherto been informed as the microbes moderately eliminating the aflatoxin in the test solution.

However, many of the reductions of aflatoxin by the microbes hereinabove mentioned are caused due to the adsorption of the aflatoxin to cell walls of the microbes (cf. J. gen. Microbiol., 54, 185 (1968); J. Bacteriol., 93,464(1967)) and besides the removal of the aflatoxin took place in an experimental test solution containing it. Referring to those publications, the removal of the aflatoxin from the cereals and nuts growing in the field and the prevention of the aflatoxin contamination in those cereals and nuts have not yet been actually accomplished by making use of the microbes hereinbefore mentioned.

Moreover, the removal of the aflatoxin from the yielded cereals and nuts may require a large amount of microbes, which is unsuitable for foodstuffs. In addition, it is difficult to completely eliminate the aflatoxin which is present within cores of the cereals and nuts. Besides, it is unknown whether or not these microbes are harmless to human being when applied to the foodstuffs. They possibly include microbes associated with hygienic problems such as pathogenicity. Moreover, there may be a species such as Streptococcus lactis which demands a specific nutritional requirement, and accordingly is unsuitable for treating the food cereals and nuts.

The present inventor has investigated microorganisms present in the soil at various regions in order to develop a method for preventing the contamination of cereals and nuts with the aflatoxin while using a microbe which is safe and harmless to the human being even when applied to the foodstuffs, and as a consequence found strains belonging to Bacillus subtilis which has so far closely been connected to the field of foodstuff industry, which strains can reduce the quantity of the aflatoxin in the aqueous solution as well as inhibit both the growth of the aflatoxin-producing fungi and their production of aflatoxin.

On the other hand, R. Mann et al. (Z. Lebensm. Unters. -Forsch., 163, 39 (1977)) describe that there are strains capable of eliminating the aflatoxin among B. subtilis (ATCC 6633 and ATCC 9372). R. Mann et al. further describe that 40 to 50% of the aflatoxin was reduced in an aflatoxin solution for 20 days. But, at such a degree of reduction, the substantial removal of the aflatoxin from the cereals and nuts growing in the field can not be expected.

D. T. Wicklow et al. (Phytopathology, 70, 761 (1980)) report that Aspergillus flavus may be inhibited in its proliferation and aflatoxin-producing activity under the co-presence of Aspergillus niger or Trichoderma viride. But the microorganisms of the present invention are bacteria, not mold such as in D. T. Wicklow et al.

SUMMARY OF THE INVENTION

The present invention provides bacterial strains of Bacillus subtilis which can inhibit the proliferation of the aflatoxin-producing fungi, suppressing the production of aflatoxin by the same fungi and reduce the quantity of the aflatoxin. In the preferred embodiments of the invention, the strains are designated as NK-330 and NK-C-3 and variants thereof.

Furthermore, the invention provides a method for preventing the aflatoxin contamination in the cereals and nuts by applying to them the strains of B. subtilis mentioned above.

DETAILED DESCRIPTIONS OF THE PREFERRED EMBODIMENTS

The strains of Bacillus subtilis, NK-330 and NK-C-3, which inhibit the growth of the aflatoxin-producing fungi and suppress the production of aflatoxin by the fungi were found during or after the completion of screening from soil samples. Their microbial characteristics are listed below.

| Characteristic | Strain NK-330 | Strain NK-C-3 |
|---|---|---|
| (1) Cell form and size | rod 0.4–0.6μ × 1.8–2.2μ | rod 0.4–0.6μ × 1.8–2.2μ |
| (2) Polymorphism of cells | none | none |
| (3) Motility | positive | positive |
| (4) Flagellation | peritrichous | peritrichous |
| (5) Spore | 0.8–1.8μ | 0.8–1.8μ |
| (6) Spores position | central | central |
| (7) Gram-stain | positive | positive |
| (8) Acid-fast stain | negative | negative |
| (9) Colony on bouillon agar plate | somewhat irregular circle white to colourless | somewhat irregular circle extremely pale brass |
| (10) Reduction of nitrate | positive | positive |
| (11) VP test | positive | positive |
| (12) Hydrolysis of starch | positive | positive |
| (13) Utilization of citric acid | positive | positive |
| (14) Oxidase | negative | positive |
| (15) Catalase | positive | positive |
| (16) Growth under aerobic condition | positive | positive |
| (17) Growth under anaerobic condition | negative | negative |
| (18) Growth at pH 5.7 | positive | positive |
| (19) Growth in 7% NaCl | positive | positive |
| (20) OF test | O (oxidative) | O (oxidative) |
| (21) Formation of acid | | |
| (21-1) D-glucose | positive | positive |
| (21-2) L-arabinose | positive | positive |
| (21-3) D-mannitol | positive | positive |
| (21-4) D-xylose | positive | positive |

Based on the above microbial characteristics, the two strains of the present invention are identified as *Bacillus subtilis*, referring to Bergy's Mannual of determinative Bacteriology, 8th and Manual for the Identification of Medical Bacteriology (Cowan & Steel), 2nd. They were deposited at Fermentation Research Institute, Tsukuba, Ibaraki in Japan, with accession numbers FERM P-9162 (date of deposit; January 30, 1987) and FERM P-9404 (date of deposit; June 6, 1987), respectively, which were then converted on November 27, 1987 to accession numbers FERM BP-1580 and FERM BP-1581, respectively, under the Budapest Treaty on the International Recognition of the Deposit of Microorganisms for the Purpose of Patent Procedure.

*B. subtilis* NK-330 (FERM BP-1580) is different from *B. subtilis* NK-C-3 (FERM BP-1581) in the colour of colony on the bouillon agar plate medium and in the reaction with oxidase.

The inhibiting activities of those two strains NK-330 and NK-C-3 to the aflatoxin-producing fungi are confirmed by streaking them on a plate medium of Potato Dextrose Agar.

Each of the strains above may effectively inhibit germination of spores of the aflatoxin-producing fungi (*A. flavus* NRRL 3357 and *A. parasiticus* NRRL 2999) on the Potato Dextrose Agar plate medium added with a liquid culture of those strains, as indicated in Examples 1 to 4 hereinunder described.

On the other hand, after inoculation of the strains according to the invention to a nutrient broth culture medium added with aflatoxin $B_1$ followed by incubation at 30° C. for one week, the strains eliminate about 85% of the aflatoxin $B_1$, as indicated in Examples 5 and 6 hereinunder described. This is far more effective as compared to R. Mann et al wherein *B. subtilis* ATCC 6633 and ATCC 9372 eliminated only about 40 to 50% of the initial aflatoxin after incubation for 3 weeks.

Furthermore, the *B. subtilis* strains of the invention may remarkably inhibit the germination of spores of the aflatoxin-producing fungi when inoculated to the sterilized peanut and corn together with the aflatoxin-producing fungi, as indicated in Examples 7 to 12. Such an inhibiting activity is not found in any other strains such as *B. subtilis* IAM 1026, as indicated in comparative Examples 12, 14, 16, 18, 20 and 22 hereinunder described.

In addition, each of the strains NK-330 and NK-C-3 has an activity to inhibit the production of aflatoxin by the aflatoxin-producing fungi in the soil and accordingly to prevent the contamination of the peanut embedded in the soil with the aflatoxin, as indicated in Examples 13 to 16 hereinunder described.

According to the present invention, the control of the aflatoxin contamination in the cereals and nuts may be accomplished by treating them before or after harvest with the strains of *B. subtilis* of the invention. For instance, by spraying over and penetrating into the field in which the cereals and nuts are growing, their protection from the aflatoxin contamination is feasible in a simple manner, and it is possible to inhibit the proliferation of the aflatoxin-producing fungi at the time of drying the crops after the harvest and to prevent the aflatoxin contamination.

In the present invention, a liquid culture of the *B. subtilis* strains with or without separated from the bacterial bodies is as well active to inhibit the growth of the aflatoxin-producing fungi and to suppress the production of aflatoxin by the fungi. Accordingly, in the present invention the application of the *B. subtilis* strains to the cereals and nuts means the applications of not only the bacterial bodies per se but also the liquid culture of the *B. subtilis* strains of the invention.

The present invention will be further described in detail with referring to Examples and Comparative Examples as below.

INHIBITING ACTIVITY TO GERMINATION OF SPORES OF *ASPERGILLUS PARASITICUS* NRRL 2999

Example 1

Into 100 ml of a Potato Dextrose liquid medium, one loopful of a strain NK-330 of *Bacillus subtilis*, FERM BP-1580, was inoculated and incubated on a rotary shaker at a temperature of 30° C. for 2 days. The bacteria thus incubated were separated by centrifugation at 8,000× g. Into the remaining liquid culture a powdery Potato Dextrose agar was added by an amount of 39.6 gr/liter, and then sterilized in an autoclave at 121° C. to prepare a plate culture medium.

Spores of *Aspergillus parasiticus* strain NRRL 2999 were smeared on the plate culture above and grown for 9 days at 25° C. The number of germinated spores and the size of colony were determined and tabulated in Table 1 below.

For comparison, the same spores were smeared on a plate culture medium prepared by adding the powdery Potato Dextrose agar by the same amount to the Potato Dextrose liquid culture medium in which the strain NK-330 was not grown (Comparative Example 1). Furthermore, a plate culture medium was prepared by using water instead of the Potato Dextrose liquid medium and adding thereto the powdery Potato Dextrose agar by the amount of 39.6 gr/liter as in Example 1, and the spores of *A. parasiticus* NRRL 2999 were smeared thereon followed by grown (Comparative Example 2).

TABLE 1

|  | Number of Germinated Spores | Size of Colony |
| --- | --- | --- |
| Example 1 | 39 | 1–2 mm |
| Comparative Example 1 | 140 | 6–10 mm |
| Comparative Example 2 | 160 | 5–12 mm |

In Example 1 wherein the strain NK-330 of *B. subtilis* was previously grown in the culture medium, the germination of the spores of the aflatoxin-producing fungi was considerably small as compared to Comparative Examples 1 and 2 wherein the strain NK-330 of *B. subtilis* was not incubated, and besides the size of colony in Example 1 was smaller than those of Comparative Examples 1 and 2. That is, the germination of the spores in Example 1 was suppressed by 72.1% as compared to Comparative Example 1 and by 75.6% as compared to Comparative Example 2 in terms of the number of germinated spores.

Example 2

Into 100 ml of a Potato Dextrose liquid medium, one loopful of a strain NK-C-3 of *Bacillus subtilis*, FERM BP-1581, was inoculated and incubated on a rotary shaker at a temperature of 30° C. for 2 days. The bacteria thus incubated were separated by centrifugation at 8,000× g. Into the remaining liquid culture a powdery Potato Dextrose agar was added by an amount of 39.6 gr/liter, and then sterilized in an autoclave at 121° C. to prepare a plate culture medium.

Spores of *Aspergillus parasiticus* strain NRRL 2999 were smeared on the plate culture above and grown for 9 days at 25° C. The number of germinated spores and the size of colony were determined and tabulated in Table 2 below.

For comparison, the same spores were smeared on a plate culture medium prepared by adding the powdery Potato Dextrose agar by the same amount to the Potato Dextrose liquid culture medium in which the strain NK-C-3 was not grown (Comparative Example 3). Furthermore, a plate culture medium was prepared by using water instead of the Potato Dextrose liquid medium and adding thereto the powdery Potato Dextrose agar by the amount of 39.6 gr/liter as in Example 2, and the spores of *A. parasiticus* NRRL 2999 were smeared thereon followed by grown (Comparative Example 4).

TABLE 2

|  | Number of Germinated Spores | Size of Colony |
| --- | --- | --- |
| Example 2 | 15 | 1–2 mm |
| Comparative Example 3 | 50 | 6–10 mm |
| Comparative Example 4 | 53 | 5–12 mm |

In Example 2 wherein the strain NK-C-3 of *B. subtilis* was previously grown in the culture medium, the germination of the spores of the aflatoxin-producing fungi was considerably small as compared to Comparative Examples 3 and 4 wherein the strain NK-C-3 of *B. subtilis* was not incubated, and besides the size of colony in Example 2 was smaller than those of Comparative Examples 3 and 4. That is, the germination of the spores in Example 2 was suppressed by 70.0% as compared to Comparative Example 3 and by 71.7% as compared to Comparative Example 4 in terms of the number of germinated spores.

INHIBITING ACTIVITY TO GERMINATION OF SPORES OF *ASPERGILLUS FLAVUS* NRRL 3357

Example 3

Into 100 ml of a Potato Dextrose liquid medium, one loopful of a strain NK-330 of *Bacillus subtilis*, FERM BP-1580, was inoculated and incubated on a rotary shaker at a temperature of 30° C. for 2 days. The bacteria thus incubated were separated by centrifugation at 8,000× g. Into the remaining liquid culture a powdery Potato Dextrose agar was added by an amount of 39.6 gr/liter, and then sterilized in an autoclave at 121° C. to prepare a plate culture medium.

Spores of *Aspergillus flavus* strain NRRL 3357 were smeared on the plate culture above and grown for 9 days at 25° C. The number of germinated spores and the size of colony were determined and tabulated in Table 3 below.

For comparison, the same spores were smeared on a plate culture medium prepared by adding the powdery Potato Dextrose agar by the same amount to the Potato Dextrose liquid culture medium in which the strain NK-330 was not grown (Comparative Example 5). Furthermore, a plate culture medium was prepared by using water instead of the Potato Dextrose liquid medium and adding thereto the powdery Potato Dextrose agar by the amount of 39.6 gr/liter as in Example 3, and the spores of *A. flavus* NRRL 3357 were smeared thereon followed by grown (Comparative Example 6).

TABLE 3

|  | Number of Germinated Spores | Size of Colony |
| --- | --- | --- |
| Example 3 | 56 | 1–2 mm |
| Comparative Example 5 | 260 | 5–7 mm |
| Comparative Example 6 | 230 | 5–9 mm |

In Example 3 wherein the strain NK-330 of *B. subtilis* was previously grown in the culture medium, the germination of the spores of the aflatoxin-producing fungi was considerably small as compared to Comparative Examples 5 and 6 wherein the strain NK-330 of *B. subtilis* was not incubated, and besides the size of colony in Example 3 was smaller than those of Comparative Examples 5 and 6. That is, the germination of the spores in Example 3 was suppressed by 78.5% as compared to Comparative Example 5 and by 75.7% as compared to Comparative Example 6 in terms of the number of germinated spores.

Example 4

Into 100 ml of a Potato Dextrose liquid medium, one loopful of a strain NK-C-3 of *Bacillus subtilis*, FERM BP-1581, was inoculated and incubated on a rotary shaker at a temperature of 30° C. for 2 days. The bacteria thus incubated were separated by centrifugation at 8,000× g. Into the remaining liquid culture a powdery Potato Dextrose agar was added by an amount of 39.6 gr/liter, and then sterilized in an autoclave at 121° C. to prepare a plate culture medium.

Spores of *Aspergillus flavus* strain NRRL 3357 were smeared on the plate culture above and grown for 9 days at 25° C. The number of germinated spores and the size of colony were determined and tabulated in Table 4 below.

For comparison, the same spores were smeared on a plate culture medium prepared by adding the powdery Potato Dextrose agar by the same amount to the Potato Dextrose liquid culture medium in which the strain NK-C-3 was not grown (Comparative Example 7). Furthermore, a plate culture medium was prepared by using water instead of the Potato Dextrose liquid medium and adding thereto the powdery Potato Dextrose agar by the amount of 39.6 gr/liter as in Example 4, and the spores of *A. flavus* NRRL 3357 were smeared thereon followed by grown (Comparative Example 8).

TABLE 4

|  | Number of Germinated Spores | Size of Colony |
| --- | --- | --- |
| Example 4 | 29 | 1–2 mm |
| Comparative Example 7 | 150 | 5–7 mm |
| Comparative Example 8 | 163 | 5–9 mm |

In Example 4 wherein the strain NK-C-3 of *B. subtilis* was previously grown in the culture medium, the germination of the spores of the aflatoxin-producing fungi was considerably small as compared to Comparative Examples 7 and 8 wherein the strain NK-C-3 of *B. subtilis* was not incubated, and besides the size of colony in Example 4 was smaller than those of Comparative Examples 7 and 8. That is, the germination of the spores in Example 4 was suppressed by 80.7% as compared to Comparative Example 7 and by 82.2% as compared to Comparative Example 8 in terms of the number of germinated spores.

ACTIVITY TO REDUCE AFLATOXIN IN AN AQUEOUS SOLUTION

Example 5

Into 5 ml of a nutrient broth culture medium, about 30 μg of aflatoxin $B_1$ dissolved in dimethylsulfoxide (DMSO) were added followed by inoculated with about $10^6$ cells of *Bacillus subtilis* strain NK-330. The amount of the aflatoxin $B_1$ in the aqueous culture medium was determined before and after the incubation under shaking at 30° C. for 7 days. The results are tabulated in Table 5.

In Comparative Example 9, the amount of the aflatoxin $B_1$ was determined in the same manner as in Example 5 but using the culture medium free from *B. subtilis* NK-330.

TABLE 5

|  | Amount of Aflatoxin $B_1$ (ppm) | |
| --- | --- | --- |
| Days | 0 | 7 |
| Example 5 | 4.7 | 0.3 |
| Comparative Example 9 | 4.7 | 2.0 |

As shown in Table 5, the amount of the aflatoxin $B_1$ in the culture medium after the incubation for 7 days in Example 5 was greatly reduced by 85% as compared to Comparative Example 9 at day 7 (reduction by 93.6% as compared to day 0), which means the activity of *B. subtilis* strain NK-330 to reduce the aflatoxin in the aqueous solution is fairly effective.

Example 6

Into 5 ml of a nutrient broth culture medium, about 30 μg of aflatoxin $B_1$ dissolved in dimethylsulfoxide (DMSO) were added followed by inoculated with about $10^6$ cells of *Bacillus subtilis* strain NK-C-3. The amount of the aflatoxin $B_1$ in the aqueous culture medium was determined before and after the incubation under shaking at 30° C. for 7 days. The results are tabulated in Table 6.

In Comparative Example 10, the amount of the aflatoxin $B_1$ was determined in the same manner as in Example 6 but using the culture medium free from *B. subtilis* NK-C-3.

TABLE 6

|  | Amount of Aflatoxin $B_1$ (ppm) | |
| --- | --- | --- |
| Days | 0 | 7 |
| Example 6 | 4.7 | 0.36 |
| Comparative Example 10 | 4.7 | 3.0 |

As shown in Table 6, the amount of the aflatoxin $B_1$ in the culture medium after the incubation for 7 days in Example 6 was greatly reduced by 88% as compared to Comparative Example 10 at day 7 (reduction by 92.3% as compared to day 0), which means the activity of *B. subtilis* strain NK-C-3 to reduce the aflatoxin in the aqueous solution is fairly effective.

INHIBITING ACTIVITY TO AFLATOXIN PRODUCTION BY *ASPERGILLUS FLAVUS* NRRL 3357 IN PEANUT

Example 7

Small grains of peanut, variety of Natalcommon, harvested in 1985 in South Africa were soaked in water for approximately 2 hours (rate of water absorption: about 50%) and thereafter 15 g of the soaked peanut were introduced into Erlenmeyer's flask followed by sterilization at 121° C. for 15 min. in an autoclave. The strain NK-330 of *Bacillus subtilis*, about 200 cells per flask, was inoculated to the sterilized peanut together with the strain NRRL 3357 of *Aspergillus flavus*, about 20 spores per flask. Incubating at 25° C., the amount of aflatoxin $B_1$ (Table 7) in the peanut was determined with the lapse of time, and it was found that in the peanut to which *B. subtilis* NK-330 was added the production of aflatoxin $B_1$ was remarkably reduced as compared to those of Comparative Example 11. That is, the strain NK-330 effectively inhibited the production of the aflatoxin $B_1$.

In this connection, Comparative Example 11 determined the amount of aflatoxin $B_1$ provided that *B. subtilis* NK-330 was not inoculated, but only *A. flavus* NRRL 3357 was inoculated.

In Comparative Example 12, *B. subtilis* strain NK-330 was replaced with *B. subtilis* strain IAM 1026. Though the strain IAM 1026 belong to *B. subtilis*, it did not inhibit the production of aflatoxin $B_1$.

TABLE 7

| | Amount of Aflatoxin $B_1$ (ppm) | | | |
|---|---|---|---|---|
| Days | 3 | 5 | 7 | |
| Ex. 7 | N.D.* | 2.1 | 2.1 | 5.5 |
| Comp. Ex. 11 | 5.0 | 55.0 | 34.9 | 25.3 |
| Comp. Ex. 12 | 1.6 | 44.8 | 62.0 | 24.3 |

*N.D. means that the aflatoxin was not detected.

Example 8

Small grains of peanut, variety of Natalcommon, harvested in 1985 in South Africa were soaked in water for approximately 2 hours (rate of water absorption: about 50%) and thereafter 15 g of the soaked peanut were introduced into Erlenmeyer's flask followed by sterilization at 121° C. for 15 mins. in an autoclave. The strain NK-C-3 of *Bacillus subtilis*, about 200 cells per flask, was inoculated to the sterilized peanut together with the strain NRRL 3357 of *Aspergillus flavus*, about 20 spores per flask. Incubating at 25° C., the amount of aflatoxin $B_1$ (Table 8) in the peanut were determined with the lapse of time, and it was found that in the peanut to which *B. subtilis* NK-C-3 was added the production of aflatoxin $B_1$ was remarkably reduced as compared to those of Comparative Example 13. That is, the strain NK-C-3 effectively inhibited the production of the aflatoxin $B_1$.

In this connection, Comparative Example 13 determined the amount of aflatoxin $B_1$ provided that *B. subtilis* NK-C-3 was not inoculated, but only *A. flavus* NRRL 3357 was inoculated.

In Comparative Example 14, *B. subtilis* strain NK-C-3 was replaced with *B. subtilis* strain IAM 1026. Though the strain IAM 1026 belongs to *B. subtilis*, it did not inhibit the production of aflatoxin $B_1$.

TABLE 8

| | Amount of Aflatoxin $B_1$ (ppm) | | | |
|---|---|---|---|---|
| Days | 3 | 5 | 7 | 9 |
| Ex. 8 | N.D.* | N.D.* | N.D.* | N.D.* |
| Comp. Ex. 13 | 6.0 | 70.0 | 42.7 | 30.1 |
| Comp. Ex. 14 | 1.2 | 43.5 | 58.3 | 27.4 |

*N.D. means that the aflatoxin was not detected.

INHIBITING ACTIVITY TO AFLATOXIN PRODUCTION BY *ASPERGILLUS PARASITICUS* NRRL 2999 IN PEANUT

Example 9

Small grains of peanut, variety of Natalcommon, harvested in 1985 in South Africa were soaked in water for approximately 2 hours (rate of water absorption: about 50%) and thereafter 15 g of the soaked peanut were introduced into Erlenmeyer's flask followed by sterilization at 121° C. for 15 mins. in an autoclave. The strain NK-330 of *Bacillus subtilis*, about 200 cells per flask, was inoculated to the sterilized peanut together with the strain NRRL 2999 of *Aspergillus parasiticus*, about 20 spores per flask. Incubating at 25° C., the amounts of aflatoxin $B_1$ (Table 9) and aflatoxin $G_1$ (Table 10) in the peanut was determined with the lapse of time, respectively, and it was found that in the peanut to which *B. subtilis* NK-330 was added the production of both aflatoxin $B_1$ and aflatoxin $G_1$ were remarkably reduced as compared to those of Comparative Example 15. That is, the strain NK-330 effectively inhibited the production of the aflatoxin $B_1$ and aflatoxin $G_1$.

In this connection, Comparative Example 15 determined the amount of aflatoxin $B_1$ and aflatoxin $G_1$ provided that *B. subtilis* NK-330 was not inoculated, but only *A. parasiticus* NRRL 2999 was inoculated.

In Comparative Example 16, *B. subtilis* strain NK-330 was replaced with *B. subtilis* strain IAM 1026. Though the strain IAM 1026 belongs to *B. subtilis*, it did not inhibit the production of aflatoxin $B_1$ and aflatoxin $G_1$.

TABLE 9

| | Amount of Aflatoxin $B_1$ (ppm) | | | |
|---|---|---|---|---|
| Days | 3 | 5 | 7 | 9 |
| Ex. 9 | N.D.* | 0.4 | 1.3 | 0.9 |
| Comp. Ex. 15 | 1.5 | 22.5 | 62.0 | 44.0 |
| Comp. Ex. 16 | 3.0 | 31.1 | 90.0 | 52.2 |

*N.D. means that the aflatoxin was not detected.

TABLE 10

| | Amount of Aflatoxin $G_1$ (ppm) | | | |
|---|---|---|---|---|
| Days | 3 | 5 | 7 | 9 |
| Ex. 9 | N.D.* | 0.3 | 2.6 | 1.8 |
| Comp. Ex. 15 | 1.6 | 44.8 | 145.0 | 60.0 |
| Comp. Ex. 16 | 4.5 | 71.0 | 252.0 | 76.9 |

*N.D. means that the aflatoxin was not detected.

Example 10

Small grains of peanut, variety of Natalcommon, harvested in 1985 in South Africa were soaked in water for approximately 2 hours (rate of water absorption: about 50%) and thereafter 15 g of the soaked peanut were introduced into Erlenmeyer's flask followed by sterilization at 121° C. for 15 mins. in an autoclave. The strain NK-C-3 of *Bacillus subtilis*, about 200 cells per flask, was inoculated to the sterilized peanut together with the strain NRRL 2999 of *Aspergillus parasiticus*, about 20 spores per flask. Incubating at 25° C., the amount of aflatoxin $B_1$ (Table 11) and aflatoxin $G_1$ (Table 12) in the peanut was determined with the lapse of time, respectively, and it was found that in the peanut to which *B. subtilis* NK-C-3 was added the production of both aflatoxin $B_1$ and aflatoxin $G_1$ was remarkably reduced as compared to those of Comparative Example 17. That is, the strain NK-C-3 effectively inhibited the production of the aflatoxin $B_1$ and aflatoxin $G_1$.

In this connection, Comparative Example 17 determined the amount of aflatoxin $B_1$ and aflatoxin $G_1$ provided that *B. subtilis* NK-C-3 was not inoculated, but only *A. parasiticus* NRRL 2999 was inoculated.

In Comparative Example 18, *B. subtilis* strain NK-C-3 was replaced with *B. subtilis* strain IAM 1026. Though the strain IAM 1026 belongs to *B. subtilis*, it did not inhibit the production of aflatoxin $B_1$ and aflatoxin $G_1$.

TABLE 11

| | Amount of Aflatoxin $B_1$ (ppm) | | | |
|---|---|---|---|---|
| Days | 3 | 5 | 7 | 9 |
| Ex. 10 | N.D.* | N.D.* | N.D.* | N.D.* |
| Comp. Ex. 17 | 5.0 | 54.0 | 34.2 | 25.1 |
| Comp. Ex. 18 | 3.0 | 31.1 | 90.0 | 52.2 |

*N.D. means that the aflatoxin was not detected.

TABLE 12

| | Amount of Aflatoxin $G_1$ (ppm) | | | |
|---|---|---|---|---|
| Days | 3 | 5 | 7 | 9 |
| Ex. 10 | N.D.* | N.D.* | N.D.* | N.D.* |
| Comp. Ex. 17 | 7.3 | 127.0 | 84.0 | 57.6 |
| Comp. Ex. 18 | 2.3 | 86.4 | 92.5 | 68.9 |

*N.D. means that the aflatoxin was not detected.

INHIBITING ACTIVITY TO AFLATOXIN PRODUCTION BY *ASPERGILLUS FLAVUS* NRRL 3357 IN CORN

Example 11

To 15 g of corn grains sterilized in the same manner as in Example 7, the strain NK-C-3 of *Bacillus subtilis*, about 200 cells per flask, was inoculated together with the strain NRRL 3357 of *Aspergillus flavus*, about 20 spores per flask. Incubating at 25° C., the amount of aflatoxin $B_1$ (Table 13) in the corn was determined with the lapse of time, and it was found that in the corn to which *B. subtilis* NK-C-3 was added the production of aflatoxin $B_1$ was remarkably reduced as compared to that of Comparative Example 19. That is, the strain NK-C-3 effectively inhibited the production of the aflatoxin $B_1$ by *A. flavus* NRRL 3357 in corn.

In this connection, Comparative Example 19 determined the amount of aflatoxin $B_1$ provided that *B. subtilis* NK-C-3 was not inoculated, but only *A. flavus* NRRL 3357 was inoculated.

In Comparative Example 20, *B. subtilis* strain NK-C-3 was replaced with *B. subtilis* strain IAM 1026. Though the strain IAM 1026 belongs to *B. subtilis*, it did not inhibit the production of aflatoxin $B_1$.

TABLE 13

| | Amount of Aflatoxin $B_1$ (ppm) | | | |
|---|---|---|---|---|
| Days | 3 | 5 | 7 | 9 |
| Ex. 11 | N.D.* | t.r.** | N.D.* | N.D.* |
| Comp. Ex. 19 | 4.8 | 63.9 | 43.8 | 37.6 |
| Comp. Ex. 20 | 1.0 | 45.8 | 51.7 | 32.2 |

*N.D. means that the aflatoxin was not detected.
**t.r. means that the detected amount was trace.

INHIBITING ACTIVITY TO AFLATOXIN PRODUCTION BY *ASPERGILLUS PARASITICUS* NRRL 2999 IN CORN

Example 12

To 15 g of corn grains sterilized in the same manner as in Example 7, the strain NK-C-3 of *Bacillus subtilis*, about 200 cells per flask, was inoculated together with the strain NRRL 2999 of *Aspergillus parasiticus*, about 20 spores per flask. Incubating at 25° C., the amounts of aflatoxin $B_1$ (Table 14) and aflatoxin $G_1$ (Table 15) in the corn were determined with the lapse of time, respectively, and it was found that in the corn to which *B. subtilis* NK-C-3 was added the production of both aflatoxin $B_1$ and aflatoxin $G_1$ was remarkably reduced as compared to those of Comparative Example 21. That is, the strain NK-C-3 effectively inhibited the production of the aflatoxin $B_1$ and aflatoxin $G_1$ by *A. parasiticus* NRRL 2999 in corn.

In this connection, Comparative Example 21 determined the amount of aflatoxin $B_1$ and aflatoxin $G_1$ provided that *B. subtilis* NK-C-3 was not inoculated, but only *A. parasiticus* NRRL 2999 was inoculated.

In Comparative Example 22, *B. subtilis* strain NK-C-3 was replaced with *B. subtilis* strain IAM 1026. Though the strain IAM 1026 belongs to *B. subtilis*, it did not inhibit the production of aflatoxin $B_1$ and aflatoxin $G_1$.

TABLE 14

| | Amount of Aflatoxin $B_1$ (ppm) | | | |
|---|---|---|---|---|
| Days | 3 | 5 | 7 | 9 |
| Ex. 12 | N.D.* | N.D.* | N.D.* | N.D.* |
| Comp. Ex. 21 | 3.1 | 67.4 | 38.7 | 30.0 |
| Comp. Ex. 22 | 1.7 | 43.9 | 59.2 | 41.3 |

*N.D. means that the aflatoxin was not detected.

TABLE 15

| | Amount of Aflatoxin $G_1$ (ppm) | | | |
|---|---|---|---|---|
| Days | 3 | 5 | 7 | 9 |
| Ex. 12 | N.D.* | N.D.* | N.D.* | N.D.* |
| Comp. Ex. 21 | 8.7 | 110.3 | 90.6 | 50.7 |
| Comp. Ex. 22 | 5.6 | 39.3 | 78.9 | 62.4 |

*N.D. means that the aflatoxin was not detected.

INHIBITING ACTIVITY TO AFLATOXIN PRODUCTION BY *ASPERGILLUS FLAVUS* NRRL 3357 IN PEANUT EMBEDDED IN SOIL

Example 13

About 25 g of commercially available culture soil was introduced into Erlenmeyer's flask of 500 ml in volume and sterilized in the autoclave at 121° C. for one hour. Then, *Aspergillus flavus* strain NRRL 3357, about 20 spores per flask, as well as *Bacillus subtilis* strain NK-330, about 200 cells per flask, was inoculated thereto. Thereafter, 15 g of the sterilized peanut of Example 7, which was harvested in South Africa was further added thereto and embedded in the culture soil. The incubation took place at 25° C. The amount of aflatoxin accumulated in the peanut were determined and the results were tabulated in Table 16.

As shown in Table 16, the production of the aflatoxin in Example 13 was remarkably inhibited as compared to Comparative Example 23 in which the strain NK-330 was not inoculated.

TABLE 16

|  | Amount of Aflatoxin (ppm) Aflatoxin $B_1$ | |
| --- | --- | --- |
| Days | 5 | 7 |
| Example 13 | 3.0 | 4.5 |
| Comparative Example 23 | 28.0 | 30.3 |

Example 14

About 25 g of commercially available culture soil was introduced into Erlenmeyer's flask of 500 ml in volume and sterilized in the autoclave at 121° C. for one hour. Then, *Aspergillus flavus* strain NRRL 3357, about 20 spores per flask, as well as *Bacillus subtilis* strain NK-C-3, about 200 cells per flask, was inoculated thereto. Thereafter, 15 g of the sterilized peanut of Example 7, which was harvested in South Africa was further added thereto and embedded in the culture soil. The incubation took place at 25° C. The amount of aflatoxin accumulated in the peanut were determined and the results were tabulated in Table 17.

As shown in Table 17, the production of the aflatoxin in Exampe 14 was remarkably inhibited as compared to Comparative Example 24 in which the strain NK-C-3 was not inoculated.

TABLE 17

|  | Amount of Aflatoxin (ppm) Aflatoxin $B_1$ | |
| --- | --- | --- |
| Days | 5 | 7 |
| Example 14 | 2.6 | 4.1 |
| Comparative Example 24 | 32.5 | 39.8 |

INHIBITING ACTIVITY TO AFLATOXIN PRODUCTION BY *ASPERGILLUS PARASITICUS* NRRL 2999 IN PEANUT EMBEDDED IN SOIL

Example 15

About 25 g of commercially available culture soil was introduced into Erlenmeyer's flask of 500 ml in volume and sterilized in the autoclave at 121° C. for one hour. Then, *Aspergillus parasiticus* strain NRRL 2999, about 20 spores per flask, as well as *Bacillus subtilis* strain NK-330, about 200 cells per flask, was inoculated thereto. Thereafter, 15 g of the sterilized peanut of Example 7, which was harvested in South Africa was further added thereto and embedded in the culture soil. The incubation took place at 25° C. The amount of aflatoxin accumulated in the peanut were determined and the results were tabulated in Table 18.

As shown in Table 18, the production of the aflatoxin in Exampe 15 was remarkably inhibited as compared to Comparative Example 25 in which the strain NK-330 was not inoculated.

TABLE 18

|  | Amount of Aflatoxin(ppm) | | | |
| --- | --- | --- | --- | --- |
|  | Aflatoxin $B_1$ | | Aflatoxin $G_1$ | |
| Days | 5 | 7 | 5 | 7 |
| Example 15 | 2.0 | 2.2 | 2.8 | 3.3 |
| Comparative | 14.0 | 12.0 | 25.1 | 22.3 |

TABLE 18-continued

|  | Amount of Aflatoxin(ppm) | |
| --- | --- | --- |
|  | Aflatoxin $B_1$ | Aflatoxin $G_1$ |
| Example 25 | | |

Example 16

About 25 g of commercially available culture soil was introduced into Erlenmeyer's flask of 500 ml in volume and sterilized in the autoclave at 121° C. for one hour. Then, *Aspergillus parasiticus* strain NRRL 2999, about 20 spores per flask, as well as *Bacillus subtilis* strain NK-C-3, about 200 cells per flask, was inoculated thereto. Thereafter, 15 g of the sterilized peanut of Example 7, which was harvested in South Africa was further added thereto and embedded in the culture soil. The incubation took place at 25° C. The amount of aflatoxin accumulated in the peanut were determined and the results were tabulated in Table 19.

As shown in Table 19, the production of the aflatoxin in Exampe 16 was remarkably inhibited as compared to Comparative Example 26 in which the strain NK-C-3 was not inoculated.

TABLE 19

|  | Amount of Aflatoxin(ppm) | | | |
| --- | --- | --- | --- | --- |
|  | Aflatoxin $B_1$ | | Aflatoxin $G_1$ | |
| Days | 5 | 7 | 5 | 7 |
| Example 16 | 1.0 | 1.3 | 2.0 | 2.2 |
| Comparative Example 26 | 18.8 | 11.3 | 24.5 | 21.4 |

INHIBITING ACTIVITY OF SUPERNATANT OF *B. SUBTILIS* NK-330 CULTURE TO AFLATOXIN PRODUCTION BY *A. PARASITICUS* NRRL 2999 IN NON-STERILIZED RAW CORN

Example 17

A pre-incubation liquid of *Bacillus subtilis* NK-330, 10 ml, was inoculated to one liter of Potato Dextrose liquid medium in a jar fermenter. The incubation of the inoculant was commenced at pH of 6.7 and maintained for 5 days under the conditions of temperature of 30° C., aeration of 500 cc/min and agitation of 150 rpm. By subjecting the resultant liquid culture to the centrifugation at 1,000 × g, the bacteria were separated to obtain a supernatant of the culture. After concentrating the supernatant in an evaporator followed by freeze-drying, 10 g of a dried residue was prepared.

The dried residue of the supernatant was added to non-autoclaved (non-sterilized) raw corn by the amount of 0.5% by weight, and then *Aspergillus parasiticus* NRRL 2999 was further added thereto by the amount of about 200 spores per flask containing 10 g of the raw corn. Then the mixture was incubated at 25° C. and the production of aflatoxin $B_1$ and aflatoxin $G_1$ was determined with the lapse of time. The results are tabulated in Tables 20 and 21.

For comparison, a control was also effected by repeating this Example 17 provided that the strain NK-330 of *B. subtilis* was not inoculated.

TABLE 20

|  | Aflatoxin $B_1$ (ppb) | | |
| --- | --- | --- | --- |
| Days | 3 | 5 | 9 |
| Ex. 17 | 7 | 15 | 8 |

TABLE 20-continued

| | Aflatoxin $B_1$ (ppb) | | |
|---|---|---|---|
| Control | 700 | 900 | 750 |

TABLE 21

| | Aflatoxin $G_1$ (ppb) | | |
|---|---|---|---|
| Days | 3 | 5 | 9 |
| Ex. 17 | 10 | 22 | 13 |
| Control | 600 | 1800 | 900 |

INHIBITING ACTIVITY OF SUPERNATANT OF B. SUBTILIS NK-330 CULTURE TO AFLATOXIN PRODUCTION BY A. FLAVUS NRRL 3357 IN NON-STERILIZED RAW CORN

Example 18

A pre-incubation liquid of *Bacillus subtilis* NK-330, 10 ml, was inoculated to one liter of Potato Dextrose liquid medium in a jar fermenter. The incubation of the inoculant was commenced at pH of 6.7 and maintained for 5 days under the conditions of temperature of 30° C., aeration of 500 cc/min and agitation of 150 rpm. By subjecting the resultant liquid culture to the centrifugation at 1,000× g, the bacteria were separated to obtain a supernatant of the culture. After concentrating the supernatant in an evaporator followed by freeze-drying, 10 g of a dried residue was prepared.

The dried residue of the supernatant was added to non-autoclaved (non-sterilized) raw corn by the amount of 0.5% by weight, and then *Aspergillus flavus* NRRL 3357 was further added thereto by the amount of about 200 spores per flask containing 10 g of the raw corn. Then the mixture was incubated at 25° C. and the production of aflatoxin $B_1$ was determined with the lapse of time. The results are tabulated in Table 22.

For comparison, a control was also effected by repeating this Example 18 provided that the strain NK-330 of *B. subtilis* was not inoculated.

TABLE 22

| | Aflatoxin $B_1$ (ppb) | | |
|---|---|---|---|
| Days | 3 | 5 | 9 |
| Ex. 18 | 10 | 20 | 17 |
| Control | 470 | 1200 | 800 |

INHIBITING ACTIVITY OF SUPERNATANT OF B. SUBTILIS NK-C-3 CULTURE TO AFLATOXIN PRODUCTION BY A. PARASITICUS NRRL 2999 IN NON-STERILIZED RAW CORN

Example 19

A pre-incubation liquid of *Bacillus subtilis* NK-C-3, 10 ml, was inoculated to one liter of Potato Dextrose liquid medium in a jar fermenter. The incubation of the inoculant was commenced at pH of 6.7 and maintained for 5 days under the conditions of temperature of 30° C., aeration of 500 cc/min and agitation of 150 rpm. By subjecting the resultant liquid culture to the centrifugation at 1,000× g, the bacteria were separated to obtain a supernatant of the culture. After concentrating the supernatant in an evaporator followed by freeze-drying, 10 g of a dried residue was prepared.

The dried residue of the supernatant was added to non-autoclaved (non-sterilized) raw corn by the amount of 0.5% by weight, and then *Aspergillus parasiticus* NRRL 2999 was further added thereto by the amount of about 200 spores per flask containing 10 g of the raw corn. Then the mixture was incubated at 25° C. and the production of aflatoxin $B_1$ and aflatoxin $G_1$ was determined with the lapse of time. The results are tabulated in Tables 23 and 24.

For comparison, a control was also effected by repeating this Example 19 provided that the strain NK-C-3 of *B. subtilis* was not inoculated.

TABLE 23

| | Aflatoxin $B_1$ (ppb) | | |
|---|---|---|---|
| Days | 3 | 5 | 9 |
| Ex. 19 | 20 | 50 | 40 |
| Control | 300 | 460 | 310 |

TABLE 24

| | Aflatoxin $G_1$ (ppb) | | |
|---|---|---|---|
| Days | 3 | 5 | 9 |
| Ex. 19 | 10 | 17 | 12 |
| Control | 180 | 580 | 400 |

INHIBITING ACTIVITY OF SUPERNATANT OF B. SUBTILIS NK-C-3 CULTURE TO AFLATOXIN PRODUCTION BY A. FLAVUS NRRL 3357 IN NON-STERILIZED RAW CORN

Example 20

A pre-incubation liquid of *Bacillus subtilis* NK-C-3, 10 ml, was inoculated to one liter of Potato Dextrose liquid medium in a jar fermenter. The incubation of the inoculant was commenced at pH of 6.7 and maintained for 5 days under the conditions of temperature of 30° C., aeration of 500 cc/min and agitation of 150 rpm. By subjecting the resultant liquid culture to the centrifugation at 1,000× g, the bacteria were separated to obtain a supernatant of the culture. After concentrating the supernatant in an evaporator followed by freeze-drying, 10 g of a dried residue was prepared.

The dried residue of the supernatant was added to non-autoclaved (non-sterilized) raw corn by the amount of 0.5% by weight, and then *Aspergillus flavus* NRRL 3357 was further added thereto by the amount of about 200 spores per flask containing 10 g of the raw corn. Then the mixture was incubated at 25° C. and the production of aflatoxin $B_1$ was determined with the lapse of time. The results are tabulated in Table 25.

For comparison, a control was also effected by repeating this Example 20 provided that the strain NK-C-3 of *B. subtilis* was not inoculated.

TABLE 25

| | Aflatoxin $B_1$ (ppb) | | |
|---|---|---|---|
| Days | 3 | 5 | 9 |
| Ex. 20 | 5 | 34 | 43 |
| Control | 280 | 720 | 640 |

What is claimed is:

1. A strain NK-330 of *Bacillus subtilis* accession number FERM BP-1580 or a variant thereof which is capable of inhibiting the growth of aflatoxin-producing fungi as well as their production of aflatoxin.

2. A strain NK-C-3 of *Bacillus subtilis* accession number FERM BP-1581 or a variant thereof which is capable of inhibiting the growth of aflatoxin-producing fungi as well as their production of aflatoxin.

3. A method for preventing an aflatoxin contamination of cereals and nuts comprising applying a strain of *Bacillus subtilis* according to either claim 1 or 2 to the cereals and nuts in an amount effective to prevent the aflatoxin contamination thereof.

4. A method as claimed in claim 3, wherein the strain of *Bacillus subtilis* is applied before or after harvest of the cereals and nuts.

5. A method as claimed in claim 3, wherein the strain of *Bacillus subtilis* is sprayed over and penetrated into the field on which the cereals and nuts are growing.

* * * * *